United States Patent [19]
Gaylord

[11] Patent Number: 6,013,045
[45] Date of Patent: Jan. 11, 2000

[54] TOUCH FASTENER STRAP AND SPLINT HAVING BUCKLE RETENTION MEANS

[75] Inventor: Robert Scott Gaylord, Matthews, N.C.

[73] Assignee: Medical Specialties Incorporated, Charlotte, N.C.

[21] Appl. No.: 09/148,929

[22] Filed: Sep. 4, 1998

[51] Int. Cl.$^7$ .................................................. A61F 13/00
[52] U.S. Cl. ............................ 602/64; 602/20; 602/60
[58] Field of Search .................. 602/5, 20, 21, 602/12, 60–65, 74–77; 128/876, 878, DIG. 15; 24/306, 442

[56] References Cited

U.S. PATENT DOCUMENTS

| | | | |
|---|---|---|---|
| 3,000,384 | 9/1961 | Piers, Jr. ............................... | 24/442 X |
| 3,827,107 | 8/1974 | Moore .......................... | 128/DIG. 15 X |
| 4,005,506 | 2/1977 | Moore .......................... | 128/DIG. 15 X |
| 4,112,521 | 9/1978 | Uke ....................................... | 24/442 X |
| 4,273,130 | 6/1981 | Simpson ...................... | 128/DIG. 15 X |
| 4,396,013 | 8/1983 | Hasslinger . | |
| 4,530,350 | 7/1985 | Brown et al. ............... | 602/3 |
| 4,570,619 | 2/1986 | Gamm . | |
| 4,996,979 | 3/1991 | Grim et al. .................... | 602/21 |
| 5,520,628 | 5/1996 | Wehr . | |
| 5,593,383 | 1/1997 | DeToro . | |
| 5,603,591 | 2/1997 | McLellan .................... | 128/DIG. 15 X |

*Primary Examiner*—Richard J. Apley
*Assistant Examiner*—Denise Pothier
*Attorney, Agent, or Firm*—Adams Law Firm, P.A.

[57] ABSTRACT

A touch fastener strap of the type which includes an elongate strap member with a buckle on a first end and complementary touch fastener elements carried by the strap member adjacent to an opposing second end. The second end of the strap member may be passed through the buckle, doubled over itself and secured in a desired position by connection of the complementary touch fasteners with each other. The improvement is a retention member carried adjacent the second end of the strap member and being deformable between a relatively thin insertion position wherein the second end of the strap member including the retention means is sufficiently thin to be inserted into and through the buckle in a first direction to form a loop, and a relatively thick retention position wherein the strap member including the retention means is sufficiently thick that it is normally retained in the buckle. The strap is also disclosed with specific reference to a wrist splint.

7 Claims, 5 Drawing Sheets

TOUCH FASTENER STRAP AND SPLINT HAVING BUCKLE RETENTION MEANS

TECHNICAL FIELD AND BACKGROUND OF THE INVENTION

This invention relates to a strap having means for retaining the strap in a buckle, and a splint, such as a wrist splint, wherein the strap is retained in the buckle during placement and removal of the splint. The strap facilitates placement of the splint on the body part with only one hand.

Numerous types of splints are known in the art of the type which can be removed and replaced by the patient. This is often necessary for bathing, dressing and adjustment of the splint. Many of these types of splints are held in place by straps which extend around the circumference of the splint and are adjusted to hold the splint in position in the correct therapeutic position and at the correct degree of tightness. These straps most often include touch fastener elements for securing the straps in the proper position. By "touch fasteners" is meant conventional hook-and-loop fasteners, or other types of fasteners which operate by means of complementary mechanical engagement of opposing surfaces.

The hooks and loops are sometimes referred to as "male" and "female" touch fastener elements. These include so-called hermaphroditic fasteners having identical complementary surfaces of upright arrow or mushroom-shaped elements which slip past each other into a locking position and are disengaged by peeling the surfaces away from each other, as well as other types.

These types of fasteners offer the advantages of being infinitely adjustable, launderable, repetitively cycled between open and closed positions numerous times, inexpensive to purchase and easy to attach to the splint. A conventional arrangement for utilizing such fasteners is to attach a simple loop-shaped buckle to the splint together with a strap of suitable length with touch fasteners on an outer-facing side. The entire outer-facing side of the strap may be comprised of loose, unbroken fibrous loops, with a relatively small patch of complementary flexible hooks positioned on the end of the strap. The end of the strap is extended around the splint, passed through the buckle, doubled back over itself to the correct fit and pressed downwardly so that the patch of hooks engages the fibrous loops.

It has been observed that some individuals have difficulty properly applying such a splint, since it may be difficult to thread the end of the strap through the relatively narrow buckle with only one hand-the hand not in the splint. This is particularly true if the buckle is attached to the splint by means of a short length of flexible webbing, as is often the case. In such circumstances the patient must hold the buckle in the correct position and insert the strap through the buckle with the same hand at the same time. This is particularly difficult if, as is often the case, the patient has injured the dominant hand and must use the other hand.

There are many other circumstances were it would be desirable to prevent the strap from slipping completely out of the buckle when it is only necessary to loosen the strap sufficiently to, for example, remove a body part from a splint or other structure. If the strap can be retained in loosened position, it is only be necessary to retighten the strap to the desired position without any need to manipulate the buckle or reinsert the strap into the buckle.

The invention of this application provides such a means of retaining the strap in the buckle. The retention means can be easily fabricated without any additional manufacturing steps and without any additional materials.

SUMMARY OF THE INVENTION

Therefore, it is an object of the invention to provide a strap having means for retaining the strap in a buckle.

It is another object of the invention to provide a strap having touch fastener elements thereon with means for retaining the strap in a buckle.

It is another object of the invention to provide a strap with means for retaining the strap in a buckle which is easy to fabricate.

It is another object of the invention to provide a strap with means for retaining the strap in a buckle in a loosened condition to facilitate manipulation of the strap.

It is another object of the invention to provide a strap with means for retaining the strap in a buckle which does not require additional fabrication steps.

It is another object of the invention to provide a strap with means for retaining the strap in a buckle which does not require additional materials.

It is another object of the invention to provide a strap with means for retaining the strap in a buckle under normal circumstances but wherein the strap can be removed if desired by exerting additional pulling force on the strap.

It is another object of the invention to provide a splint, such as a wrist splint, wherein the strap is retained in the buckle during placement and removal of the splint.

It is another object of the invention to provide a splint, such as a wrist splint, wherein the splint can be easily placed on the wrist, adjusted, and removed from the wrist with one hand.

It is another object of the invention to provide a splint having a strap with means for retaining the strap in a buckle in a loosened condition to facilitate, with one hand, placement of the splint on the body part to be protected, to facilitate adjustment of the splint, and to facilitate removal of the splint.

These and other objects of the present invention are achieved in the preferred embodiments disclosed below by providing a touch fastener strap of the type which includes an elongate strap member with a buckle on a first end and complementary touch fastener elements carried by the strap member adjacent to an opposing second end. The second end of the strap member may be passed through the buckle, doubled over itself and secured in a desired position by connection of the complementary touch fasteners with each other. The improvement comprises retention means carried adjacent the second end of the strap member and being deformable between a relatively thin insertion position wherein the second end of the strap member including the retention means is sufficiently thin to be inserted into and through the buckle in a first direction to form a loop, and a relatively thick retention position wherein the strap member including the retention means is sufficiently thick so that it is normally retained in the buckle.

According to one preferred embodiment of the invention, said retention means comprises a deformable member cooperating with the second end of the strap member and extending outwardly from the plane of the strap member in a direction whereby the deformable member is deformed downwardly into the plane of the strap member during insertion of the second end of the strap into and through the buckle and is deformed outwardly away from the plane of the strap member during movement of the strap from the buckle.

According to another preferred embodiment of the invention, said retention means comprises a length of touch fastener material carried by the strap member to form a double-thickness portion, and an end edge of the double-thickness portion extends outwardly from the plane of the strap member in a direction whereby the end edge of the double-thickness portion is deformed downwardly into the plane of the strap member during insertion of the second end of the strap into and through the buckle, and is deformed outwardly away from the plane of the strap member during removal of the strap from the buckle.

According to yet another preferred embodiment of the invention, said end edge is defined by a line of transverse stitches extending across the width of said strap member.

According to yet another preferred embodiment of the invention, one side of said strap member is covered with touch fastener elements comprising loose, fibrous loops.

Preferably, one side of said strap member is covered with touch fastener elements comprising loose, fibrous loops and a complementary patch of flexible hooks.

According to one preferred embodiment of the invention, a splint product is provided for immobilizing a body part and comprises a support dimensioned to fit around the body part to be immobilized. A touch fastener strap member and buckle are carried by the support in opposed relation wherein the strap member may be passed through the buckle, doubled over itself and secured in a desired position by connection of complementary touch fasteners carried by the strap member with each other to secure the support in position around the body part. The improvement comprises retention means carried in closely spaced-apart relation to a free end of the strap member. The retention means is deformable between a relatively thin insertion position wherein the free end of the strap member including the retention means is sufficiently thin to be inserted into and through the buckle in a first direction, and a relatively thick retention position wherein the strap member including the retention member is sufficiently thick that it is normally retained in the buckle.

According to another preferred embodiment of the invention, the retention means comprises a deformable member cooperating with the second end of the strap member and extending outwardly from the plane of the strap member in a direction whereby the deformable member is deformed downwardly into the plane of the strap member during insertion of the second end of the strap into and through the buckle and is deformed outwardly away from the plane of the strap member during removal of the strap from the buckle.

According to yet another preferred embodiment of the invention, the retention means of the splint comprises a length of touch fastener material carried by the strap member to form a double-thickness portion, and further wherein an end edge of the double-thickness portion extends outwardly from the plane of the strap member in a direction whereby the end edge of the double-thickness portion is deformed downwardly into the plane of the strap member during insertion of the second end of the strap into and through the buckle, and is deformed outwardly away from the plane of the strap member during removal of the strap from the buckle.

According to yet another preferred embodiment of the invention, said end edge of the strap member of the splint is defined by a line of transverse stitches extending across the width of said strap member.

According to yet another preferred embodiment of the invention, one side of said strap member is covered with touch fastener elements comprising loose, fibrous loops.

According to yet another preferred embodiment of the invention, one side of said strap member is covered with touch fastener elements comprising loose, fibrous loops and a complementary patch of flexible hooks.

According to yet another preferred embodiment of the invention, said splint comprises a wrist splint.

According to yet another preferred embodiment of the invention, the wrist splint includes hand fastening means for being positioned between the thumb and forefinger to secure the wrist splint to the hand, and arm fastening means for being positioned around the arm to secure the wrist splint around the arm.

According to yet another preferred embodiment of the invention, the wrist splint support is tubular and is placed on the wrist by inserting the hand and wrist into the support from one end.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
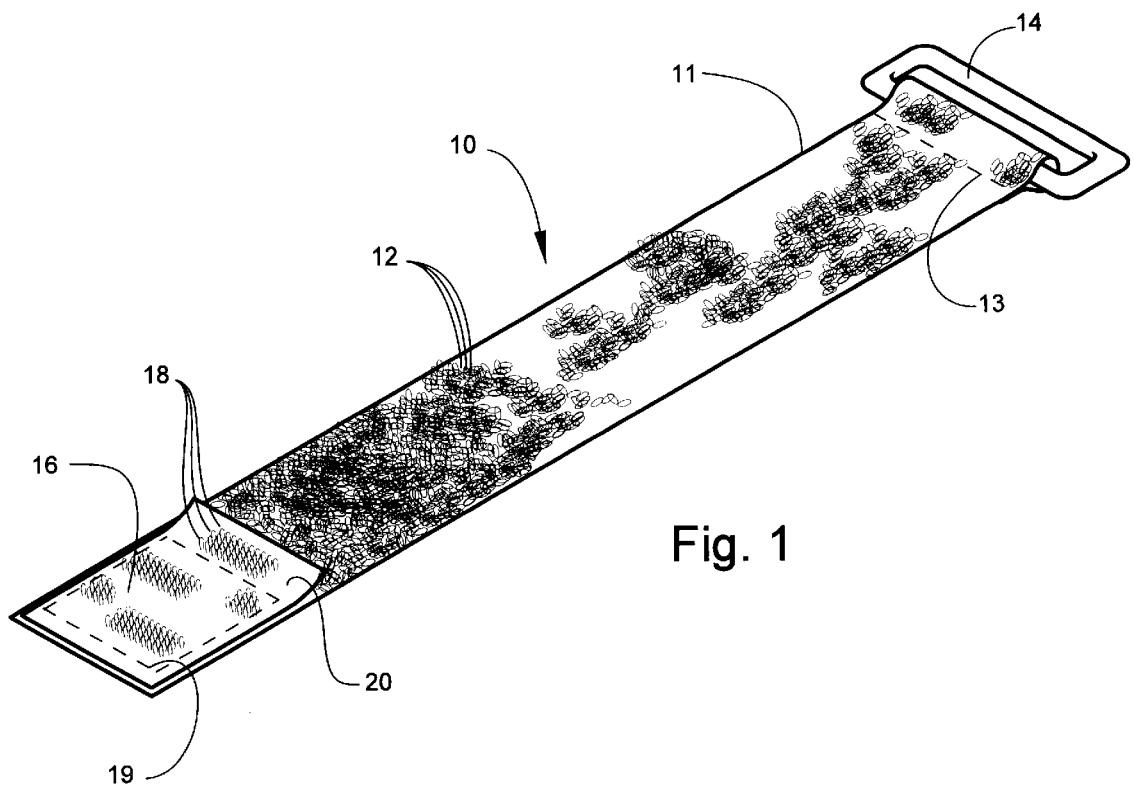
FIG. 1 is a perspective view of a strap according to a preferred embodiment of the invention.

Referring now specifically to the drawings, a strap according to the present invention is illustrated in FIG. 1 and shown generally at reference numeral 10. The strap 10 is formed of an elongate strap member 11 of suitable length for the intended use. Strap member 11 is typically a woven or knitted tape with a loose, unbroken fibrous surface on one side formed of a multitude of loose loops 12. The loops 12 form one-half of a touch fastener system.

A buckle 14 is secured to one end of the strap member 11 by passing one end of the strap member 11 through the buckle 14 and doubling the strap member 11 over on itself. The doubled portion of the strap member 11 is then stitched or with sewing stitches 13 or otherwise joined, such as by ultrasonic welding, to secure the buckle 14 to the end of the strap member 11.

A woven or knitted patch 16 having a multitude of hooks 18 is stitched or ultrasonically welded onto the end area of strap member 11 opposite the buckle 14. Note that the patch 16 is stitched to the same side of the strap member 11 as carries the loops 12 with sewing stitches 19.

As is also shown in FIG. 1, the stitches 19 are placed on the patch 16 so as to leave a short retention member 20 extending along the strap member 11 in the direction of the buckle 14. The compression of the patch 16 into the strap member 11 caused by the stitches 19 causes the retention member 20 to angle outwardly slightly away from the plane of the strap member 11, and it is this feature which permits the invention to work so simply and effectively.

The angle of the retention member 20 is such that when the strap member 11 is being passed into and through the buckle 14, the retention member 20 is easily depressed back onto the surface of the strap member 11. Thus, the retention member 20 and the strap member are collectively relatively thin and thus pass through the buckle 14 without resistance.

Figure 2:
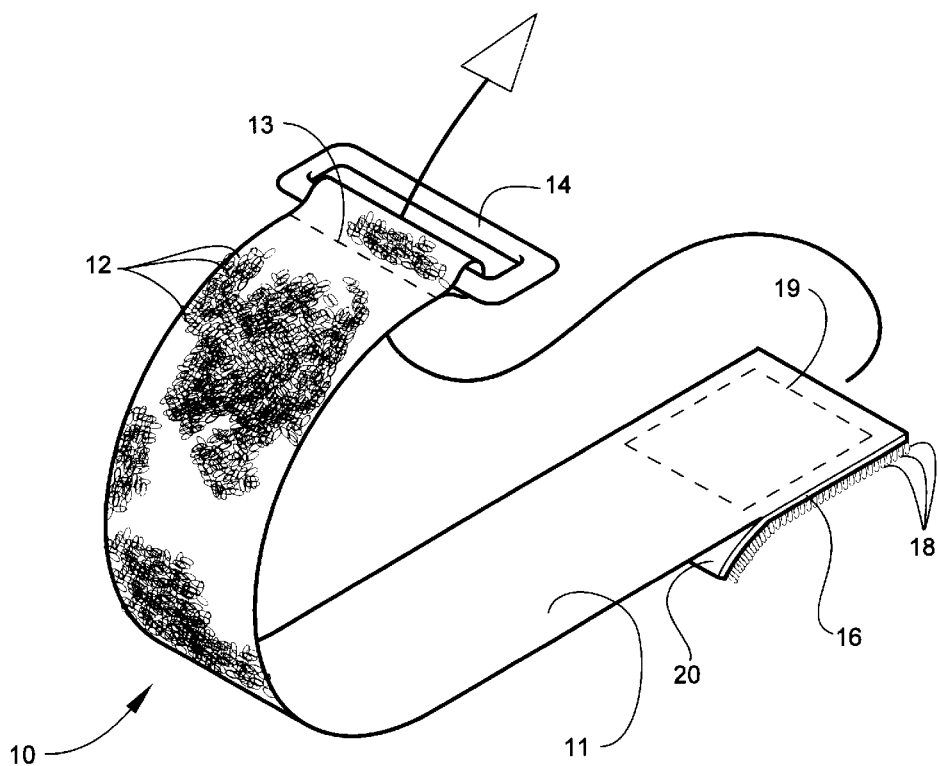
FIG. 2 is a perspective view of the strap shown in FIG. 1 being formed into a loop.
Figure 3:
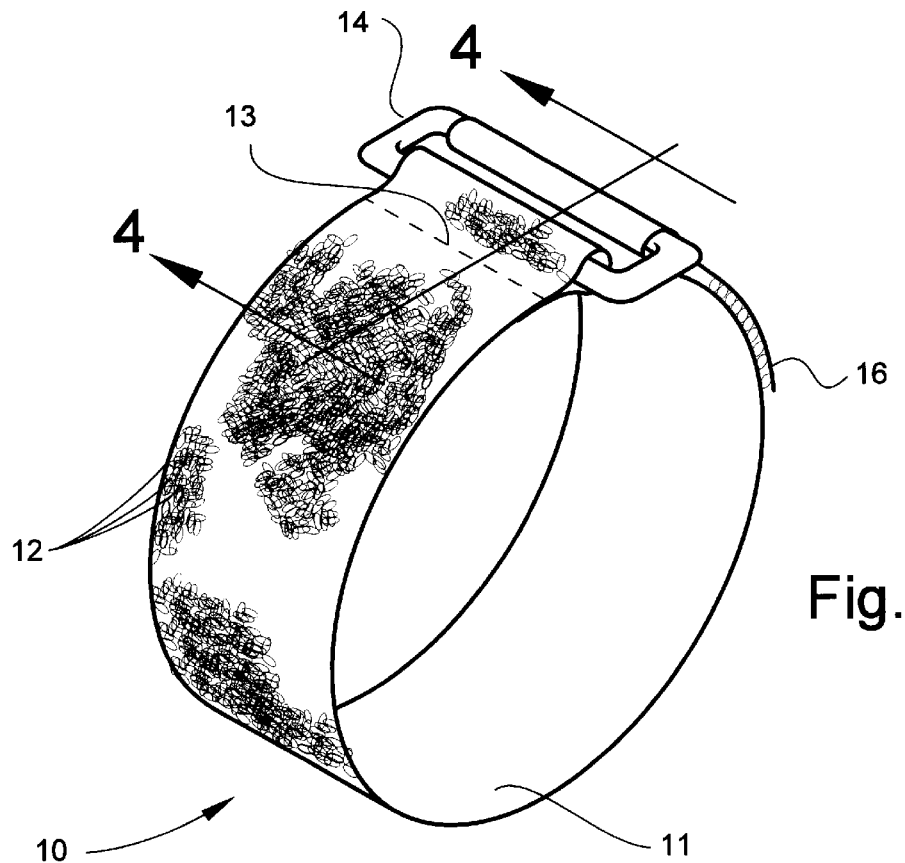
FIG. 3 is a perspective view of the strap shown in FIG. 1 after being formed into a loop.
Figure 4:
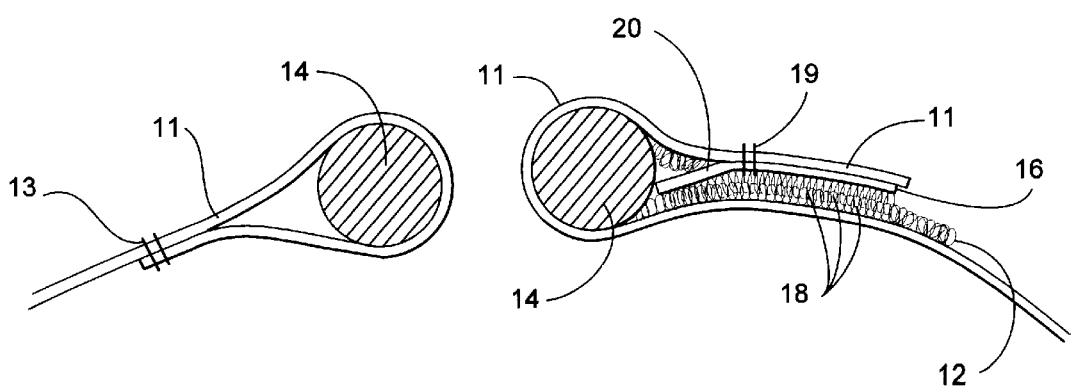
FIG. 4 is a vertical cross-section of the end portion of a strap according to an embodiment of the invention.

As is shown in FIG. 2, the second end of the strap member 11—the one with the patch 16—is passed through the buckle 14 and doubled back over itself. After being properly adjusted, the patch 16 is depressed downwardly onto the loops 12, fastening the strap member 11 into a desired diameter. The position of the patch 16 and the angle of the retention member 20 is shown in a somewhat exaggerated manner in FIG. 4. Note that the retention member 20 continues to perform its gripping function even though it is attached to the strap member only by the line of stitching 19.

Figure 5:
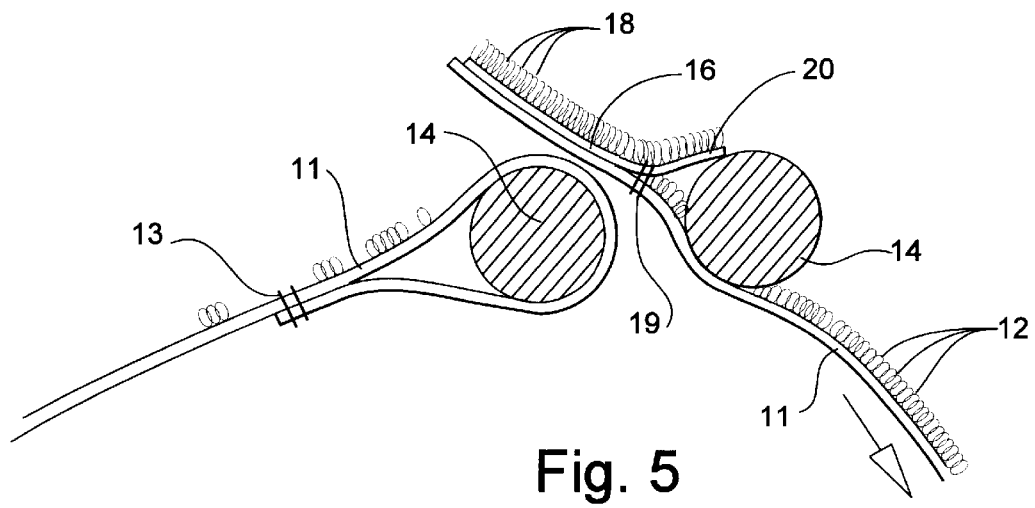
FIG. 5 is a vertical cross-section of the end portion of a strap showing retention of the strap member in the buckle.

Referring now to FIG. 5, the function of the retention member 20 is illustrated. As is shown, when the strap member 11 is loose, the angle of the retention member 20 is such that it catches on the buckle 14 and normally prevents the second end of the strap member 11 from slipping back through the buckle 14. The retention member 20, while capable of flexing, is sufficiently stiff to resist the weight of the strap member 11 as it tries to slide through the buckle 14. On the other hand, in a situation where the user desires to completely remove the second end of the strap member 11 from the buckle 14, force applied to the strap member 11 will cause the retention member 20 to fold back onto the patch 16, allowing the second end of the strap member 11 to pass through the buckle 14. In effect, the thickness of the retention member 20 and the strap member 11 is sufficiently great to prevent unaided passage of the strap member completely out of the buckle 14, and thus normally defines a relatively thick retention position.

Figure 6:
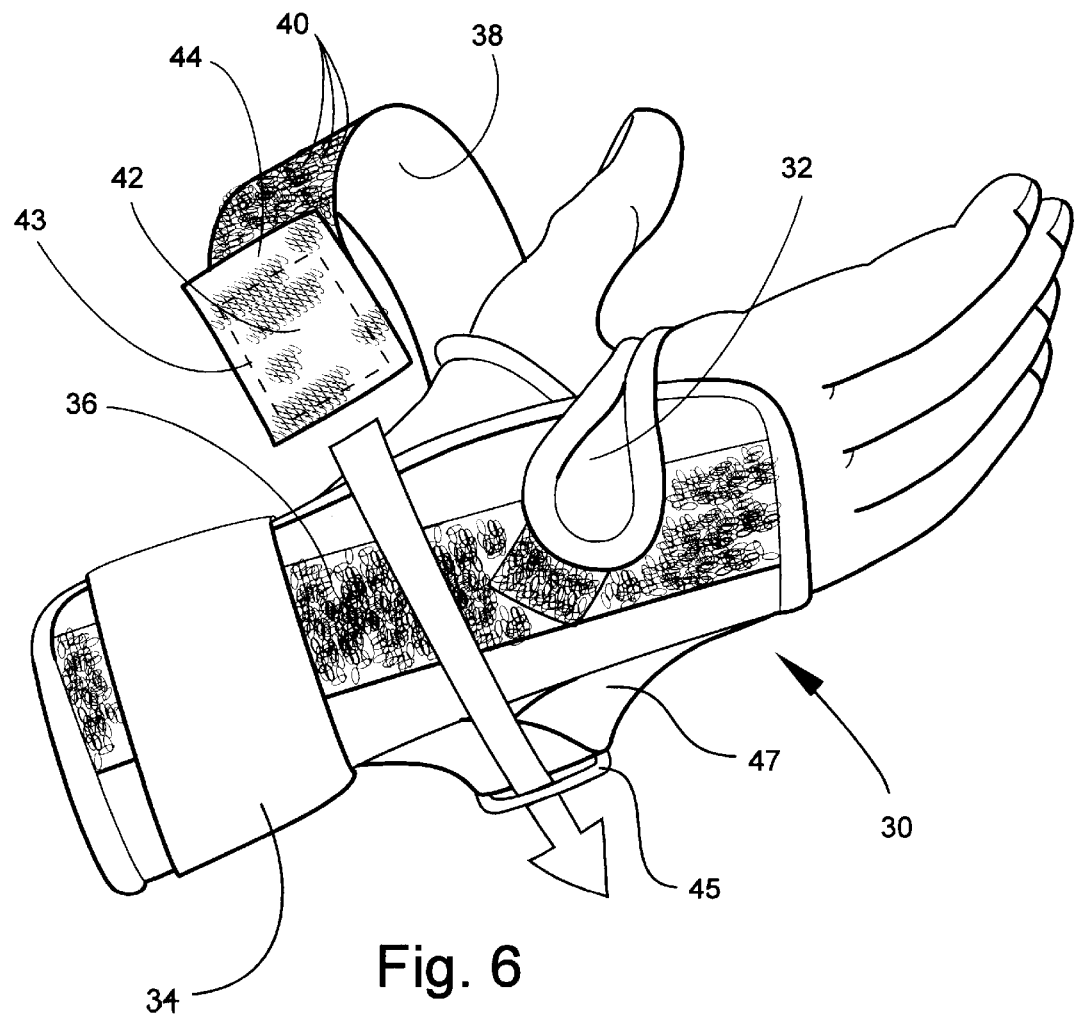
FIGS. 6–9 are perspective, environmental sequential views of a wrist splint according to an embodiment of the invention.
Figure 7:
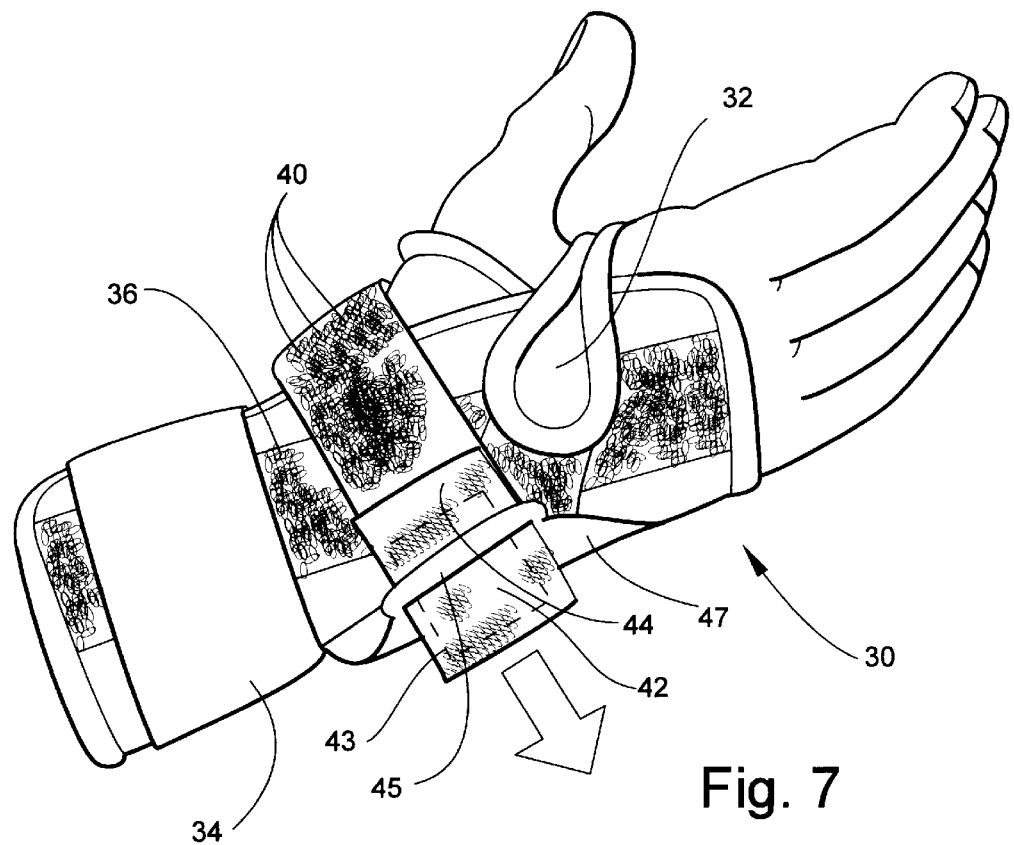
Figure 8:
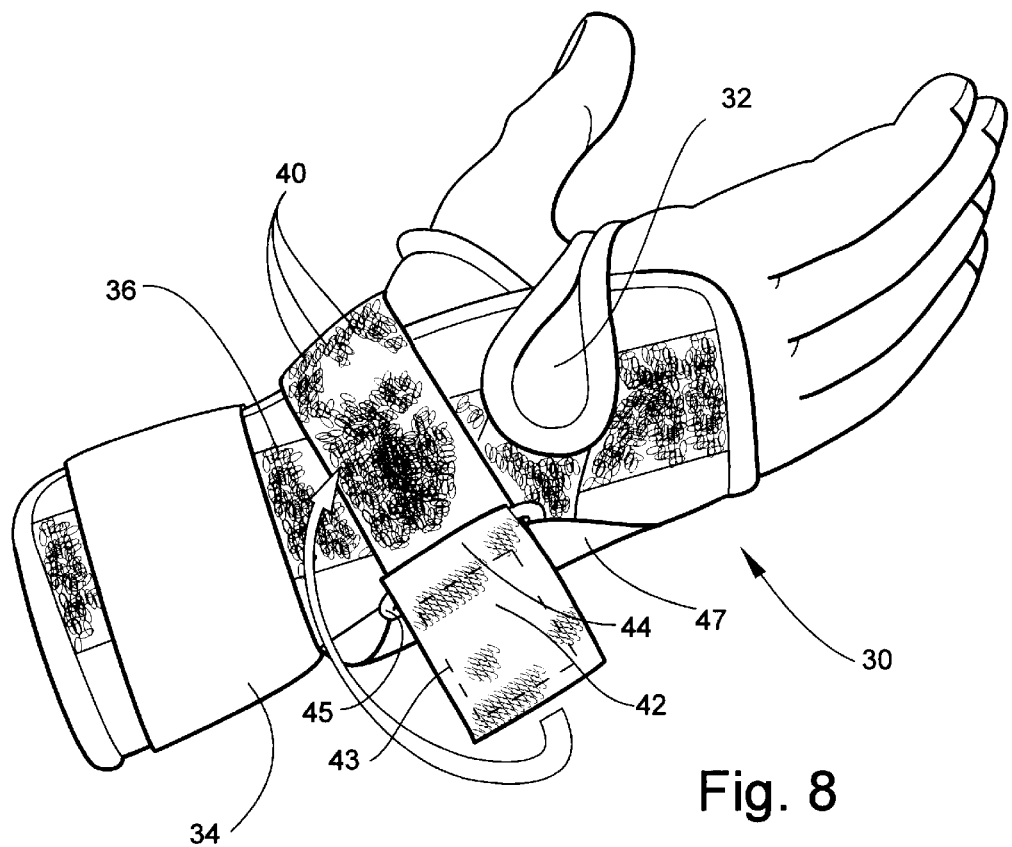

The strap 10 illustrated in FIGS. 1–4 has wide application to secure any object by encircling it and some support adjacent to it. A specific application according to a variation of the invention is shown in FIGS. 6–9. As is shown in FIG. 6, a tubular wrist splint 30 is secured to the wrist by extending the hand into and through the splint 30 so that the splint 30 extends from approximately where the palm of the hand joins the base of the fingers to the lower arm above the wrist. The wrist splint 30 shown in FIGS. 69 is generally typical of prior art splints insofar as it includes hand fastening means comprising a strap 32 and arm fastening means 34 for securing the splint 30 to the hand and arm at the desired degree of tightness. An elongate strip of loose, non-woven fibrous loops 36 cooperates with patches of flexible hooks (not shown) on the underside of the straps 32 and 34 to retain the straps 32 and 34 in the desired position.

In accordance with the invention, a centrally-located wrist strap member 38 provides support directly over the wrist of the wearer. As is shown in FIG. 6, strap member 38 is attached to the underside of the splint 30 and extends around to the top of the splint 30. The strap member 38 has loose, nonwoven fibrous loops 40 on the outwardly-facing surface and a patch 42 of flexible hooks attached by sewing stitches 43 positioned on the end of the outwardly-facing surface, as shown. The sewing stitches 43 are positioned to form a retention member 44. The retention member 44 functions in the same manner as the retention member 20 in FIGS. 1–5, and reference back to those Figures is made for the purpose of further explanation.

Figure 9:
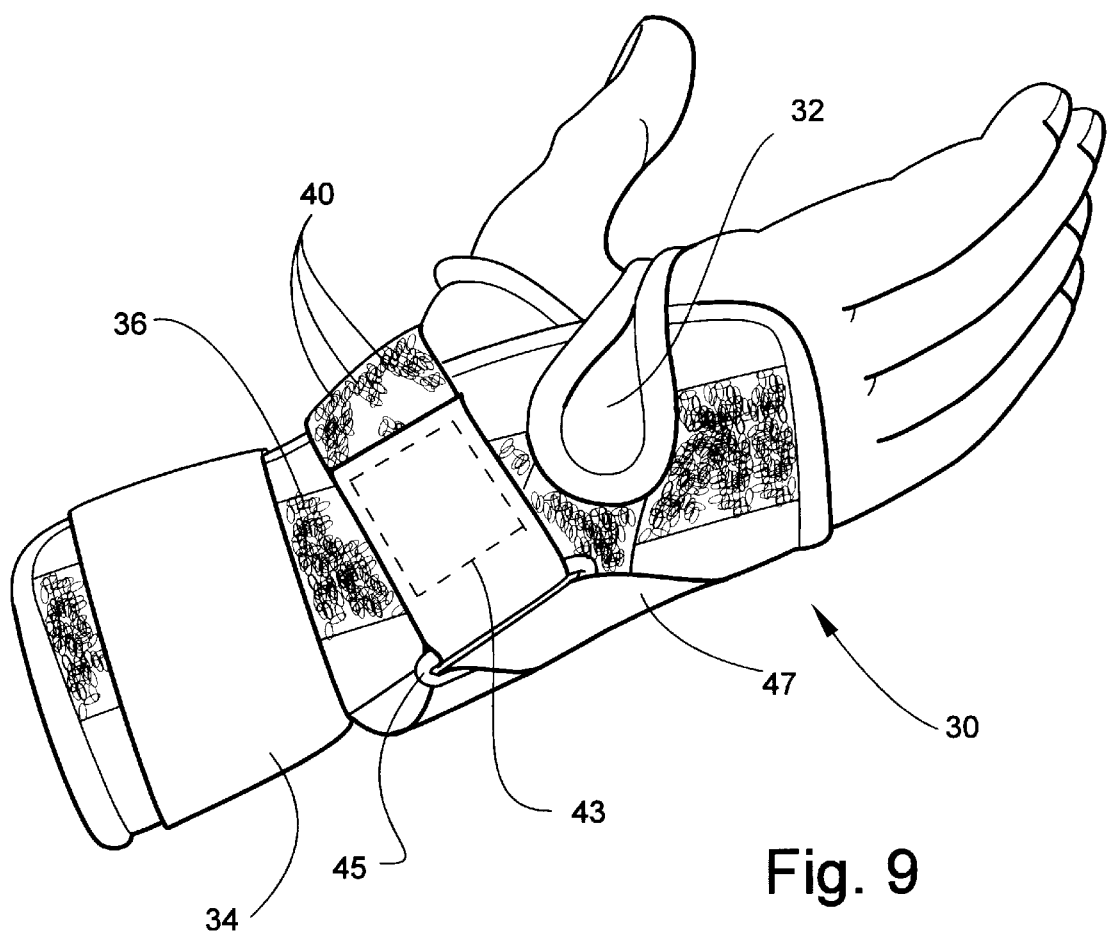

A buckle 45 is attached to splint 30 by a short length of elastic webbing 47, opposing ends of which are secured at spaced-apart locations on the lateral side of the splint 30. As is shown in FIGS. 6–9, the strap member 38 is extended through the buckle 45 (FIGS. 6 and 7); doubled back on itself (FIG. 8); and the patch 42 depressed into the fibrous loops 40 to secure the strap member 38 in the desired position (FIG. 9). Straps 32 and 34 and strap member 38 are independently adjustable.

To remove the splint, straps 32 and 34 and strap member 38 are detached, loosening the splint 30 so the hand can be withdrawn. Retention member 44 functions to prevent the strap member 38 from being withdrawn entirely from the buckle 45. Thus, when the wearer is ready to replace the splint 30, the hand is re-inserted into the splint 30 and the straps 32 and 34 re-attached. Since the strap member 38 has been retained in the buckle 45, it is not necessary to rethread the strap member 38 into the buckle 45 with one hand, or obtain help from someone else. Rather, it is a simple matter to grasp the end of the strap member 38 and pull it back into the proper position for reattachment to the loops 40 on the strap member 38.

Should the wearer wish to remove the strap 38 from the buckle 45, a tug at the strap 38 will cause the retention member 44 to fold back against the patch 42, allowing the end of the strap 38 to pass through the buckle 45.

A touch fastener strap and a splint having buckle retention means is described above. Various details of the invention may be changed without departing from its scope. Furthermore, the foregoing description of the preferred embodiment of the invention and the best mode for practicing the invention are provided for the purpose of illustration only and not for the purpose of limitation-the invention being defined by the claims.

I claim:

1. In a splint product for immobilizing a body part, comprising a support dimensioned to fit around the body part to be immobilized, a touch fastener strap member and buckle carried by the support in opposed relation wherein the strap member may be passed through the buckle, folded over itself and secured in a desired position by connection of complementary touch fasteners carried by the strap member with each other to secure the support in position around the body part, the improvement comprising retention means comprises a loose flap on a free end of the strap member, said retention means being deformable between:

(a) a relatively thin insertion position wherein the free end of the strap member including the retention means is sufficiently thin to be inserted into and through the buckle in a first direction; and (b) a relatively thick retention position wherein the strap member is doubled on itself to form a double-thickness portion wherein said loose flap of the retention means extends away from the plane of the strap member in a direction whereby the loose flap is deformed toward the plane of the strap member during insertion of the free end of the strap member into and through the buckle, and is deformed away from the plane of the strap member on itself to define a third thickness portion during removal of the strap through the buckle.

2. In a splint product according to claim 1, wherein said loose flap is defined by a line of transverse stitches extending across the width of said strap member.

3. In a splint product according to claim 1 or 2, wherein one side of said strap member is covered with touch fastener elements comprising loose, fibrous loops.

4. In a splint product according to claim 1 or 2, wherein one side of said strap member is covered with touch fastener elements comprising loose, fibrous loops and a complementary patch of flexible hooks.

5. In a splint product according to claim 1, wherein said splint product comprises a wrist splint.

6. In a splint product according to claim 5, wherein said wrist splint includes hand fastening means for being positioned between the thumb and forefinger to secure the wrist splint to the hand, and arm fastening means for being positioned around the arm to secure the wrist splint around the arm.

7. In a splint product according to claim 5, wherein said support is tubular and is placed on the wrist by inserting the hand and wrist into the support from one end.

* * * * *